United States Patent [19]
Song

[11] Patent Number: 5,400,666
[45] Date of Patent: Mar. 28, 1995

[54] METHODS AND APPARATUS FOR AUTOMATED ON-COLUMN INJECTION USING A SLENDER NEEDLE

[75] Inventor: Wei J. Song, Wilmington, Del.

[73] Assignee: Hewlett-Packard Company, Palo Alto, Calif.

[21] Appl. No.: 252,955

[22] Filed: Jun. 1, 1994

Related U.S. Application Data

[63] Continuation of Ser. No. 971,443, Nov. 4, 1992, abandoned.

[51] Int. Cl.⁶ .............................................. G01N 35/06
[52] U.S. Cl. ............................... 73/864.21; 73/864.87
[58] Field of Search ................. 73/19.02, 23.41, 61.55, 73/61.56, 863.11, 864.21-864.25, 864.74, 864.81-864.87

[56] References Cited

U.S. PATENT DOCUMENTS

| | | | |
|---|---|---|---|
| 3,201,994 | 8/1965 | Adams | 73/864.74 |
| 3,976,078 | 8/1976 | Toriello | 606/189 |
| 4,393,792 | 7/1983 | St Clair | 112/2.1 |
| 4,518,387 | 5/1985 | Murphy et al. | 604/187 |
| 4,605,073 | 8/1986 | Nilsson et al. | 173/51 |
| 4,713,974 | 12/1987 | Stone | 73/864.86 |
| 4,926,119 | 5/1990 | Propkopp | 324/158 P |
| 5,013,305 | 5/1991 | Opie et al. | 604/192 |
| 5,020,458 | 6/1991 | Michelberger | 112/7 |
| 5,032,151 | 7/1991 | Klein et al. | 95/17 |

*Primary Examiner*—Robert Raevis
*Attorney, Agent, or Firm*—Mark Z. Dudley

[57] ABSTRACT

Methods and apparatus for preventing the failure of slender syringe needles used for on column injection in gas chromatographs are disclosed. A needle holder designed to support the needle precludes bucking deflection beyond the maximum allowable value. In a preferred embodiment, the needle used is a tapered needle that has a proximal diameter and a distal diameter that is smaller that the proximal diameter. In these embodiments, the diameter of the bore through the needle holder is slightly larger than the proximal diameter to permit the full insertion of the entire needle structure. The needle holder bore diameter is sufficiently small, however, to preclude catastrophic failure due to buckling.

6 Claims, 2 Drawing Sheets

METHODS AND APPARATUS FOR AUTOMATED ON-COLUMN INJECTION USING A SLENDER NEEDLE

CROSS REFERENCE TO RELATED APPLICATION

This is a continuation of application Ser. No. 07/971,443, filed on Nov. 4, 1992, now abandoned.

The present invention relates to an advancement in the art of chromatography, and more particularly, to a gas chromatographic system for on-column injection into columns of relatively small inner diameters.

BACKGROUND OF THE INVENTION

In the analysis of a sample compound using a gas chromatograph a supply of inert carrier gas (mobile phase) is continually passed as a stream through a heated column containing porous sorptive media (stationary phase). In the past, chromatographic systems have incorporated columns formed as hollow capillary tubes having an inner diameter in the range of few hundred microns ($\mu$m, $1 \times 10^{-6}$ meters). In such systems, a sample of the subject mixture is injected into the mobile phase stream and passed through the capillary column, which is typically positioned within an oven. As the subject mixture passes through the capillary column, it separates into its various components. Separation is due primarily to differences in the volatility characteristics of each sample component with respect to the temperature in the column. Column temperature is primarily regulated by oven temperature. A detector, positioned at the outlet end of the capillary column, detects each of the separated components as they exit the column.

Column efficiency (typically referred to in terms of theoretical plates) of capillary columns is dependent on both column length and diameter. A column having a larger inner diameter must be longer than a column having a smaller inner diameter in order to achieve comparable efficiency. As will be appreciated by those of ordinary skill, greater column length results in longer analysis times, which can effect sensitivity. However, shorter columns with relatively narrow column inner diameters have been limited in relation to the techniques available for sample injection. Consequently, certain prior gas chromatographic analyses have been a compromise between sensitivity and efficiency in relation to the column and injection technique utilized.

Injecting sample directly into column with a diameter less than 530 $\mu$m requires a slender syringe needle. For example, a needle with an outer diameter less than 0.240 mm (240 $\mu$m) is used for a 250 $\mu$m column. As a lower limit, the slender section of the needle has to be long enough to inject a sample into the section of the column inside the gas chromatograph. However, as explained in U.S. Pat. No. 5,032,151—Klein et al., which is incorporated herein by reference, a slender syringe needle can be bent during the piercing of vial caps or while passing through the inlet septum of the column. There are two needle failure modes: buckling and compression. When the needle punches the vial cap, if the piercing force is low, the deflection, y, of the needle is smaller, than a certain value, $y_m$, the needle will return to its original equilibrium position (i.e., a straight needle) and be stable. As the piercing force increases (for example, with a thicker vial cap), the deflection becomes larger. When the deflection exceeds $y_m$ the needle will move away from its original equilibrium position and fail. In other words, this unstable situation will cause the needle to buckle. The limit or maximum deflection, $y_m$, depends on the geometry and material of the needle. Compression failure is another mode of needle failure. If the compression stress of the needle exceeds the yield stress of its material, the needle will fail. However, since the syringe needle is slender, buckling failure will occur under a much lower stress than that for compression failure. Accordingly, buckling is the most frequent failure mode for a typical syringe needle.

The critical load, $P_{cr}$, of a given needle, below which the needle would not buckle, can theoretically be calculated using Euler's formula:

$$\frac{P_{cr}}{A} = \frac{\pi^2 E}{(L_e/R)^2}$$

Where A, $L_e$ and R are the area, effective length and radius of gyration of the needle. The modulus of elasticity of the needle, E, is a material constant. The Euler equation set forth above, however, is derived from a more generalized equation, and presumes that the boundary conditions include both ends of the needle being hinged, i.e., unable to resist a bending moment. On the other hand, if it is assumed that both ends of the needle are fixed, the Euler equation becomes:

$$\frac{P_{cr}}{A} = \frac{4\pi^2 E}{(L_e/R)^2},$$

indicating that a change in boundary conditions increased the critical load by a factor of four.

Because a needle passing through a septum and into a column represents a dynamic system having end conditions that are neither fixed nor hinged, the true value of $P_{cr}$ is difficult to determine theoretically, and, accordingly, it is difficult to determine a maximum theoretical deflection value, $Y_m$. However, those of ordinary skill will realize that there are values of $L_e$ for a given diameter needle that will deflect elastically and return to a stable position. These values are readily determined empirically.

It has been found, however, that for a relatively narrow column, such as the slender needles discussed above, buckling phenomenon reduce the maximum useful length to less than that which is required for successful injection, even if the maximum elastic deflection, $y_m$, is permitted. Therefore, it would be desirable to increase the length of a slender syringe needle to a length useful for injection that would not catastrophically fail under load.

In the past, several improvements were made to reduce the chance of needle buckling. A tapered needle improves needle strength by reducing its effective length. Finally, the use of thin membrane vial caps and inlet septa with pre-determined through-holes significantly reduce the piercing force. For example, U.S. Pat. No. 5,032,151—Klein et al., incorporated herein by reference, discloses a system for on-column injection using columns having diameters less than 530 $\mu$m. This reference explains that the buckling problem described above limits the diameter of chromatographic columns even though narrower columns will provide better results. It is disclosed that columns having diameters less than 530 $\mu$m can be effectively utilized by reducing the effective length of the narrowest portion of the injection needle, thereby maximizing resistance to buckling. A preferred embodiment discloses a capillary column having an inner diameter of 320 μm, and a needle that has a distal portion with an outer diameter of 0.2286 mm (228.6 μm).

Despite the advances disclosed in the Klein et al. reference, there remains a long-felt, but as yet unfilled need to provide methods and apparatus whereby syringe needles of relatively narrow cross-section can be utilized in conjunction with slender columns for gas chromatography. Additionally, it would be particularly desirable to provide methods and apparatus whereby needles of even smaller diameter than those disclosed by Klein et al. could be so used. It is therefore an object of the present invention to provide methods and apparatus for substantially eliminating the buckling of slender syringe needles while retaining an overall length sufficient to be used for on-column injection. Additionally, due to the high number of samples processed, it would be desirable to permit relatively inexpensive septa and vial caps to be used, even though they generate a greater resistive force than other types of septa and caps. It is therefore a further object of the present invention to provide such a system whereby conventional vial caps and other septa may be penetrated using a relatively slender needle.

SUMMARY OF THE INVENTION

These and other objects are attained by the methods and apparatus of the present invention, which substantially eliminates the buckling failure of syringe needles. The small section of the tapered needle, which is to be inserted into the column is confined in a small bore of needle support. The wall of the bore provides support to the needle so the maximum deflection of the needle would never exceed $y_m$ and buckling will never occur. The needle can stand much larger piercing force because compression failure occurs at much higher stress level. The system of the present invention is more robust against failure, and can use standard, thick vial caps, which give better sealing and are cheaper.

DETAILED DESCRIPTION OF THE PREFERRED EMBODIMENTS

The methods and apparatus described herein are preferably used in conjunction with a gas chromatograph such as that described in U.S. Pat. No. 5,032,151—Klein et al., referenced above and incorporated herein by reference. Those of ordinary skill will be familiar with the construction and operation of this and other types of similar equipment. Accordingly, although the preferred embodiments disclosed herein are illustrated with reference to the system disclosed in the Klein et al. patent, it will be understood that the present invention is not limited to any particular type of apparatus.

Figure 1:
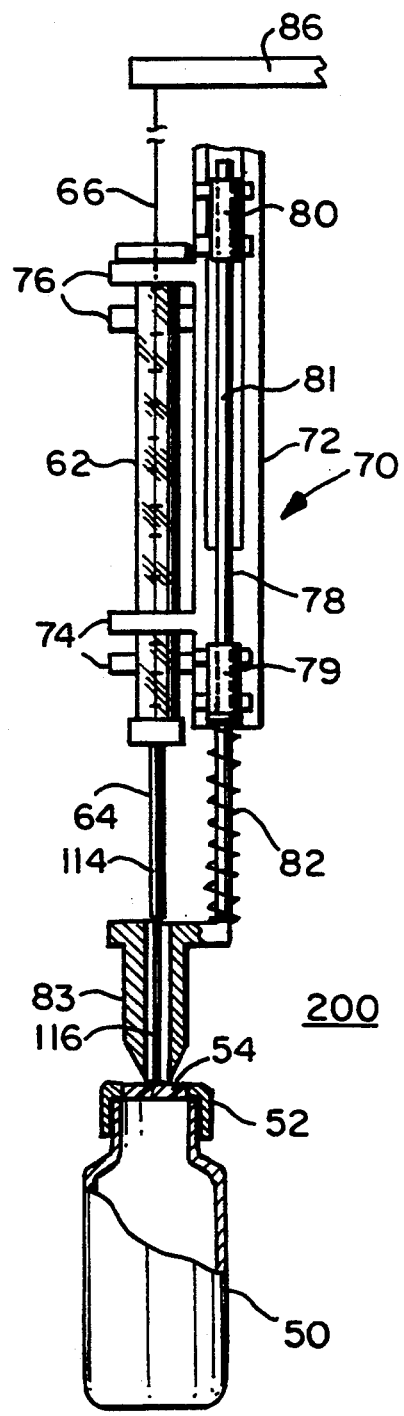
FIG. 1 is a broken away elevation view, partially in cross-section of a preferred embodiment of the present invention, immediately prior to insertion into a sample vial.

Referring now to FIG. 1, their is shown a broken away view, partially in cross-section, of an apparatus 200 made in accordance with the present invention. Except as noted herein, the function of this apparatus is substantially as that shown in the above-referenced Klein et al. patent. Injection is made using a syringe 62 that includes a needle 64 and a plunger 66. It will be appreciated that as the plunger 66 is pulled from the syringe 62, a sample is drawn into the syringe 62 through the needle 64. Conversely, as the plunger 66 is pushed into the syringe 62, any sample contained therein will be ejected from the needle 64. FIG. 1 illustrates the initial stage of a chromatographic process, wherein a sample is to be withdrawn from a sample container 50. As well known to those of ordinary skill, the sample container 50 is typically closed by a cap 52 that includes a pierceable section or septum 54. The sample container 50 is shown partially broken away for purposes of illustration.

As illustrated in FIG. 1, a positioning mechanism 70 includes a base member 72 that is capable of axial movement relative to the sample container 50. Two opposed pairs of finger 74,76 are attached to the base member 72 and serve to hold the syringe 62 in a fixed relation relative to the base member 72. Thus, it will be appreciated that axial movement of the base 72 will result in axial movement of the syringe 62. A rod 78 is slidingly attached to the base 72 in a fashion that permits axial movement in relation to movement of the base 72. The rod 78 is attached to the base by two collars 79,80 that are both fixed in relation to the base 72. A spring 82 serves to maintain the rod 78 in an extended position shown in FIG. 1. Such an extended position is achieved by fixing one end of the spring 82 to the base 72 by any suitable means and by placing the other end against a needle support 83 that is securely attached to the end of the rod 78. As will be described in greater detail below, the needle support 83 is designed to restrict the deflection of the needle 64 and thereby prevent its failure due to buckling.

Also shown in FIG. 1 is an arm 86 that is attached to the plunger 66 and serves to move the plunger 66 into or out of the cylinder 62. Although not shown, the arm 86 can be attached to any suitable movement mechanism capable of providing axial movement of the plunger 66. Such a mechanism is described in U.S. Pat. No. 4,615,226 and is also similar to the mechanism of the HP 7673A automated injection device manufactured and sold by the Hewlett-Packard Corporation of Palo Alto, Calif.

The needle 64 shown in FIG. 1 is most preferably a tapered needle having a base portion 114 and an end portion 116. The base portion 114 is the first diameter and the end portion 116 is the second, smaller diameter. The outer diameter of the end portion 116 is less than the inner diameter of a column (not shown in FIG. 1) into which the sample will eventually be inserted. By providing a tapered needle 64, the end portion 116 can have a minimum diameter while maximizing its resistance to bending and buckling. As pointed out in the Klein et al. patent referenced above, the buckling strength of the needle 64 is increased by reducing the effective length of the most slender portion of the structure, the end portion 116. In preferred embodiments, the outside diameter of the base portion 114 is between about 125 μm and 530 μm.

Figure 2:
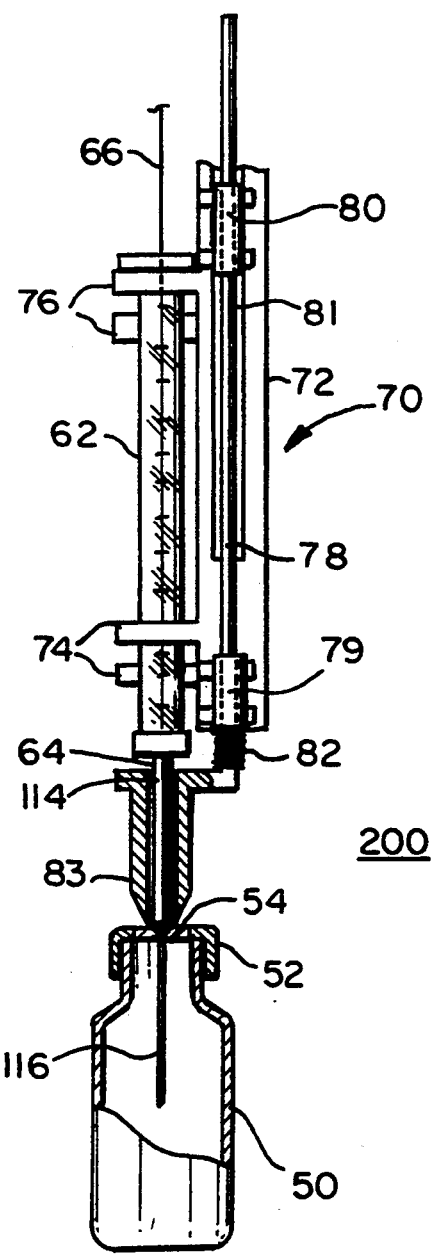
FIG. 2 depicts the apparatus of FIG. 1 immediately after insertion into the sample vial.

Referring now to FIG. 2 it is seen that the apparatus described with reference to FIG. 1 can be used to withdraw a sample from the sample container 50. As explained above, the needle support 83 of the present invention is designed to support the needle 64, and in particular the slender end portion 116 thereof. As seen by comparing FIG. 1 and FIG. 2, the end portion 116 is initially disposed within a hollow bore formed within the needle holder 83. The diameter of this hollow bore is sized so that as the needle 64 is urged into and through the septum 54 of the cap 52 and into the sample container 50 any potential buckling is controlled. In other words, if the diameter of the bore is chosen to be less than the maximum allowable deflection, failure due to buckling cannot occur. However, as seen in FIG. 2, the minimum diameter of the bore should be slightly larger than the outside diameter of the base portion 114 of the needle 64, so that the needle 64, and in particular the end portion 116 can extend for its full useful length into the sample container 50 as shown.

As one example of a preferred embodiment, a needle 64 may be constructed that has a base portion 114 having an outside diameter of 0.0185 inches (0.47 mm) and having an end portion 116 with a diameter of 0.0091 inches (0.23 mm). For such a needle, it has been found that a needle support 83 having a bore therethrough of a diameter of about 0.0193 inches (0.49 mm) is able to prevent the end portion 116 from buckling beyond the maximum allowable deflection, $Y_m$, while still permitting the base portion 114 to slide therethrough.

Thus, in summary, as will be appreciated by those of ordinary skill, the apparatus disclosed in FIGS. 1-2 permits a syringe needle 64 to be inserted through a septum 54 and into a sample container 50 and allows a sample therein to be withdrawn. The needle support 83 prevents buckling from causing the needle 64 to fail, and so long as to the force required to penetrate the septum does not exceed the maximum allowable compressive force, a needle having a smaller diameter at its end portion 116 then previously possible may be used. Moreover, sample containers 50 having conventional caps 52 and septa 54 may be used in such embodiments, eliminating the expense and complexity of specially designed sample container for use in conjunction with such thinner needles.

Figure 3:
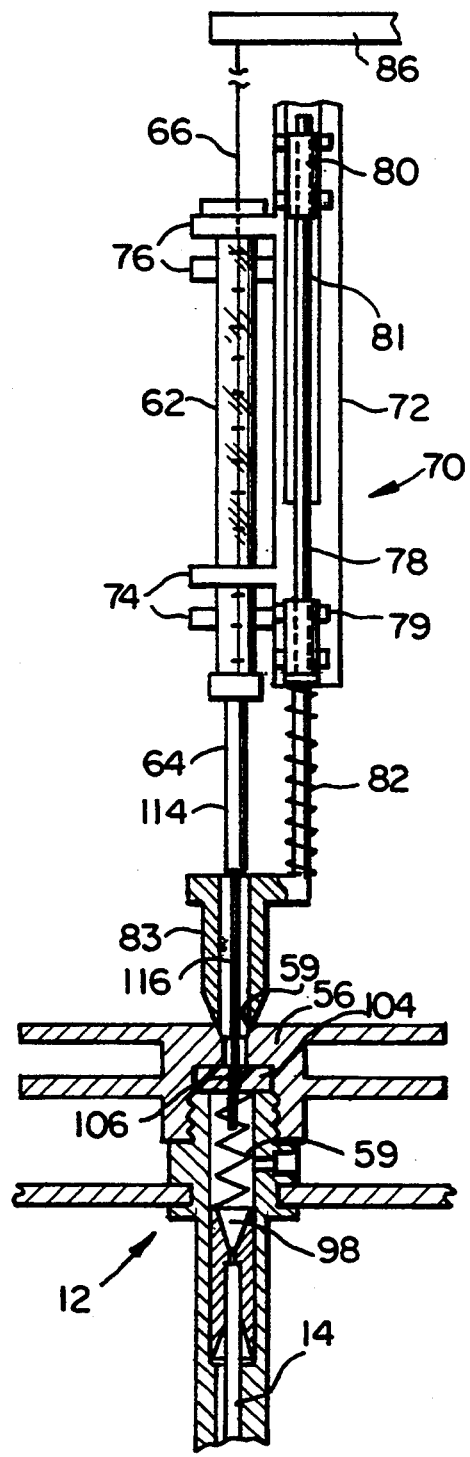
FIG. 3 is a broken away elevation view, partially in cross-section of a preferred embodiment of the present invention, immediately prior to insertion into a column.
Figure 4:
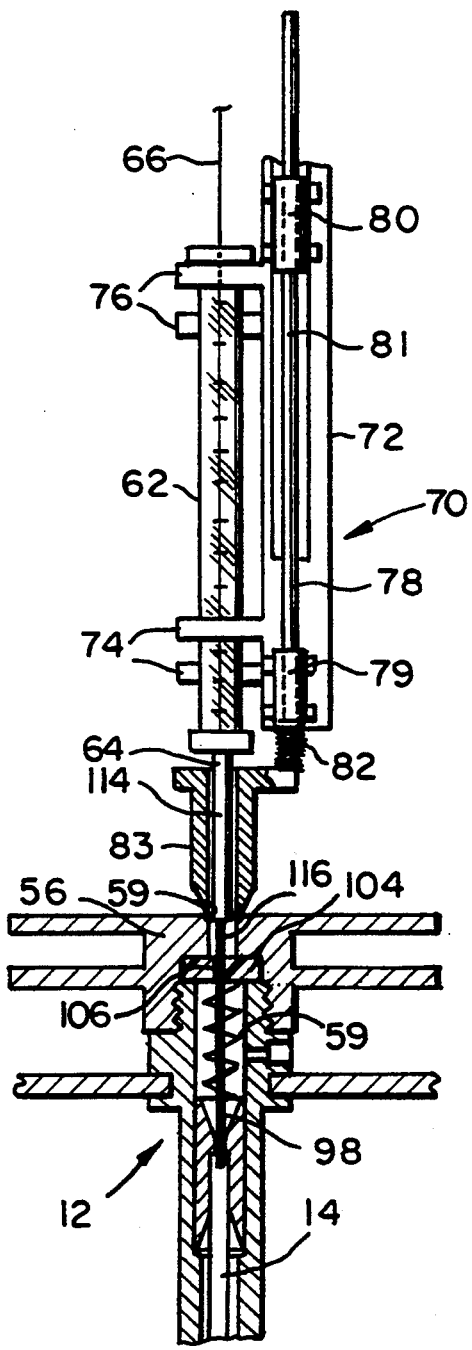
FIG. 4 depicts the apparatus of FIG. 3 immediately after insertion into the column.

Referring now to FIGS. 3-4 the apparatus illustrated in FIGS. 1-2 is again illustrated, however, an inlet assembly 12 as illustrated in FIGS. 2-5 of U.S. Pat. No. 5,032,151—Klein et al., as referenced above has been substituted for the sample container 50. As will be readily appreciated by those of ordinary skill, the inlet 12 illustrated is a typical embodiment of such an apparatus, and numerous variations of such apparatus are well known. The present invention is useful with a wide variety of inlets and other such structures that are used to place a syringe needle in communication with a capillary column or the like.

As seen in FIG. 3, the needle support 83 is engaged with the passage 59 formed in the upper body portion 56 of the inlet apparatus 12. The passage 59 is connected to a septum 104. Preferably, the septum 104 does not have an orifice and the needle 64 punctures the septum 104. However, those of ordinary skill will readily appreciate that providing an orifice 106 in the septum 104 will reduce the resistive force and permit somewhat easier penetration. As seen by comparing FIGS. 3-4 the needle support 83 again provides support for the end portion 116 of the needle 64 as it is inserted through the septum 104 and the passage 59 and ultimately into a capillary column 14 after passing through the frusto-conically shaped inlet end 98 of the passage 59. Thus, the present invention also permits the slender needle described above to be effectively used to inject a sample into a capillary column of commensurately smaller diameter.

Although certain embodiments of the present invention have been set forth above with particularity, and with reference to U.S. Pat. No. 5,032,151—Klein et al., the present invention is not limited to the precise embodiments disclosed. Upon review of the instant specification, those of ordinary skill will readily appreciate that there are numerous adaptations, modifications and variations of the methods and apparatus disclosed herein that will be used for a variety of chromatographic equipment. Both the structure of the syringe and of the chromatographic inlet to the capillary column may vary widely depending on the equipment being used and the chromatographic process being undertaken. Accordingly, in order to determine the full scope of the present invention reference should be made to the appended claims.

What is claimed is:

1. A system for performing on-column injection of a sample into a chromatographic device, comprising:
    a syringe;
    a hollow needle connected to the syringe for passage of the sample therethrough, the needle having a base portion and an end portion, the end portion having an outside diameter less than that of the base portion; and
    a needle support having a bore therethrough, the diameter of said bore being sufficient to enclose and thereby restrict the deflection of at least one of said base portion and end portion so enclosed to less than a predetermined maximum deflection $y_m$; and
    a positioning mechanism operatively connected to the needle and the needle support for effecting automated relative axial movement of the needle with respect to the needle support, said movement being between a first position wherein the end portion of the needle is substantially enclosed within the needle support, and a second position wherein the end portion is extended substantially outside the needle support.

2. The system of claim 1, wherein bore has a bore diameter that is at least 20 µm larger than the outside diameter of the needle.

3. The system of claim 2, wherein the outside diameter is less than 530 µm.

4. The system of claim 2, wherein the outside diameter is less than 300 µm.

5. The system of claim 2, wherein the outside diameter is between about 125 µm and 530 µm.

6. The system of claim 2, wherein the outside diameter is about 0.0091 inches (230 µm) and the bore diameter is about 0.0193 inches (490 µm).

* * * * *